United States Patent [19]

Ritacco et al.

[11] Patent Number: 4,737,292

[45] Date of Patent: Apr. 12, 1988

[54] HPLC COLUMN AND A COLUMN PACKING METHOD

[75] Inventors: Robert P. Ritacco, Jamestown; Thomas W. Hampton, Narraganset, both of R.I.

[73] Assignee: Separations Technology, Inc., Wakefield, R.I.

[21] Appl. No.: 43,701

[22] Filed: Apr. 29, 1987

Related U.S. Application Data

[63] Continuation-in-part of Ser. No. 871,076, Jun. 5, 1986, abandoned.

[51] Int. Cl.⁴ ............................................. B01D 15/08
[52] U.S. Cl. .................................. 210/656; 210/198.2; 55/67; 55/386
[58] Field of Search ....................... 55/67, 386; 141/73, 141/80; 210/656, 657, 659, 198.2; 222/319

[56] References Cited

U.S. PATENT DOCUMENTS

| | | | |
|---|---|---|---|
| 1,042,909 | 10/1912 | Graham | 222/319 |
| 1,079,848 | 4/1913 | Ellingwood | 222/319 |
| 1,244,585 | 10/1917 | Case | 222/319 |
| 1,615,765 | 1/1927 | Laws | 222/319 |
| 1,863,871 | 6/1932 | Packwood | 222/319 |
| 3,306,502 | 2/1967 | Harris | 222/319 |
| 3,487,938 | 1/1970 | Patterson | 210/198.2 |
| 3,511,377 | 5/1970 | Hrdina | 210/198.2 |
| 4,131,547 | 12/1978 | Michel | 210/198.2 |
| 4,250,035 | 12/1981 | McDonald | 210/198.2 |
| 4,522,715 | 6/1985 | Walters | 210/198.2 |
| 4,582,608 | 4/1986 | Ritacco | 210/656 |

FOREIGN PATENT DOCUMENTS

| | | | |
|---|---|---|---|
| 2600622 | 7/1977 | Fed. Rep. of Germany | 210/198.2 |
| 2656737 | 7/1977 | Fed. Rep. of Germany | 210/198.2 |
| 2704883 | 8/1978 | Fed. Rep. of Germany | 210/198.2 |
| 509591 | 8/1981 | Switzerland | 210/198.2 |
| 837363 | 6/1960 | United Kingdom | 210/198.2 |
| 868586 | 9/1981 | U.S.S.R. | 210/198.2 |

Primary Examiner—Ernest G. Therkorn
Attorney, Agent, or Firm—Donald Brown

[57] ABSTRACT

This invention relates to a column for use in preparative HPLC so structured as to insure a reproducible packing bed uniformity regardless of the particle size of the medium used.

11 Claims, 5 Drawing Sheets

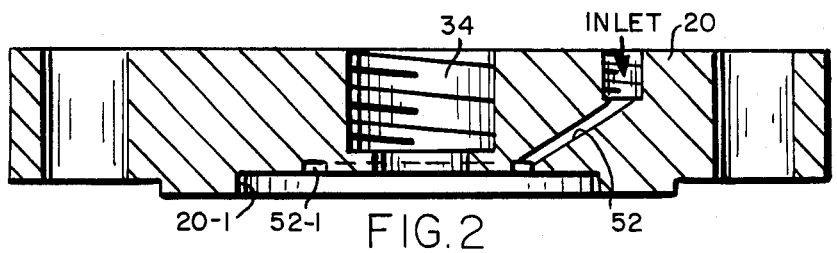
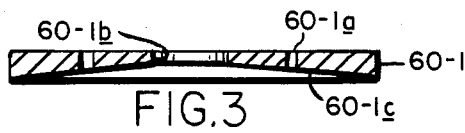
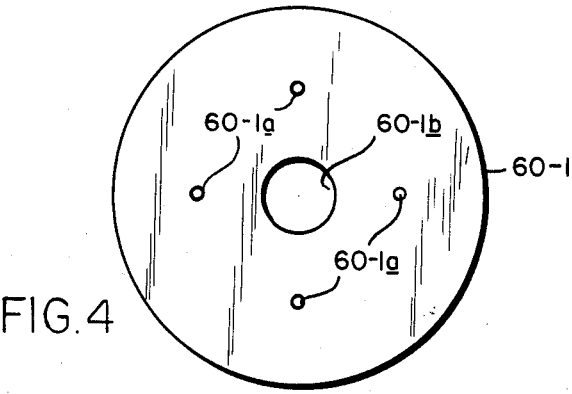
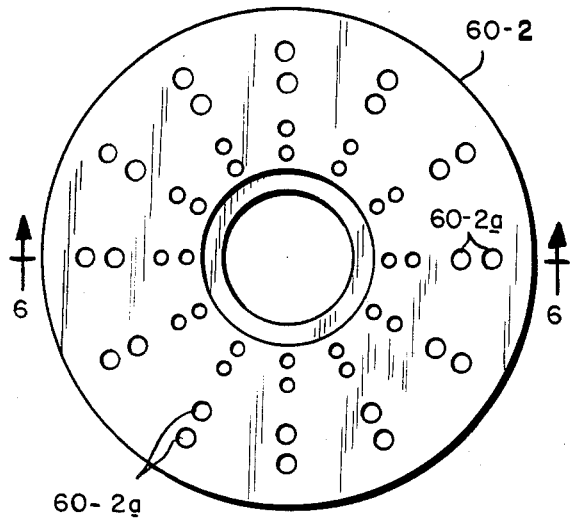
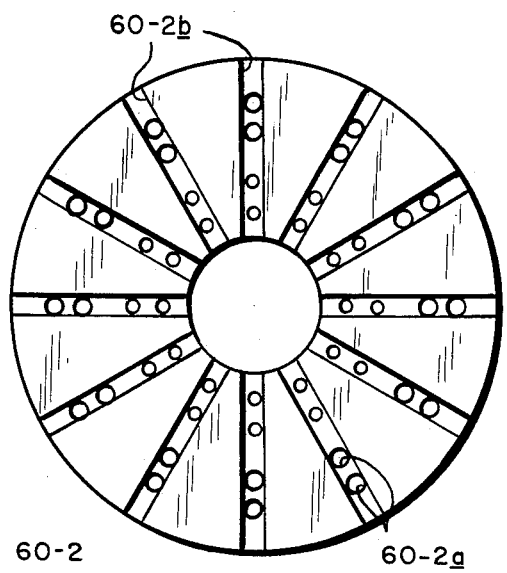
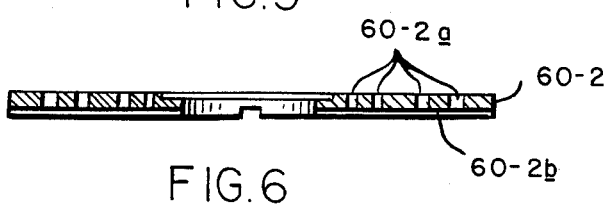

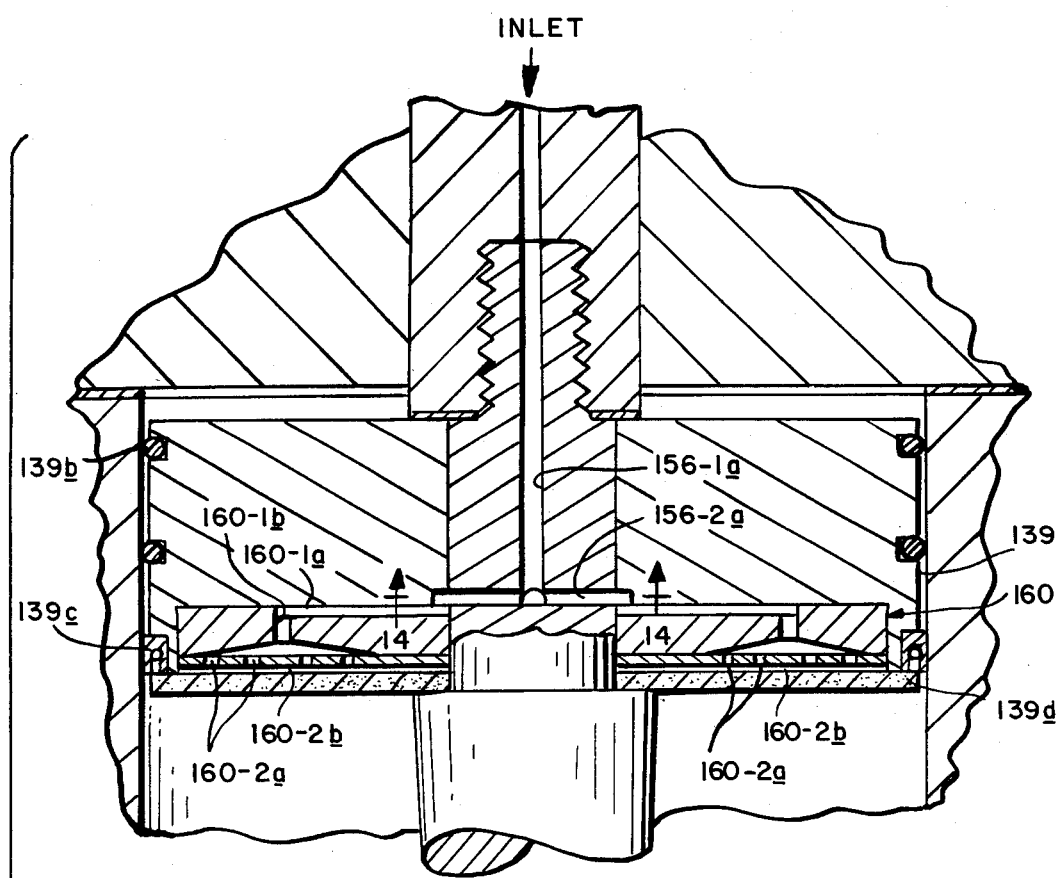
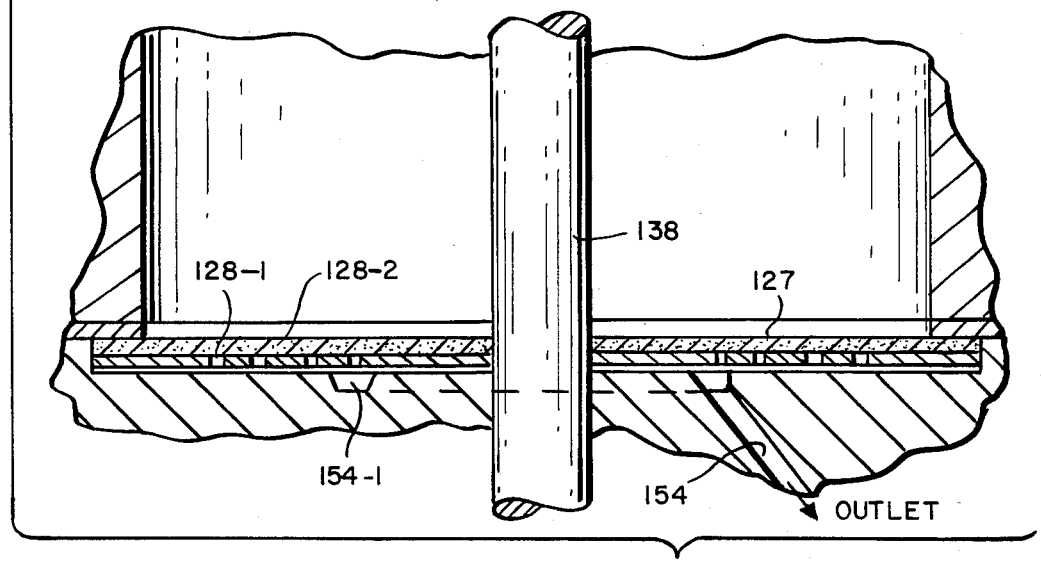
FIG. 13
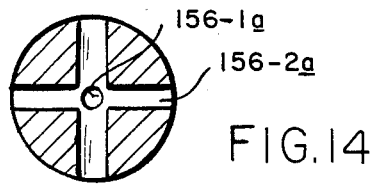
FIG. 14

HPLC COLUMN AND A COLUMN PACKING METHOD

PRIOR APPLICATION

This application is a continuation in part of U.S. patent application Ser. No. 871,076 filed June 5, 1986, now abandoned.

BACKGROUND OF THE INVENTION

The most common preparative HPLC columns have simply been tubes into which a packing medium is introduced and the bed allowed to settle by means of vibration and solvent flow. This method has been cumbersome and has had problems in the area of reproducibility. Other methods have been introduced to overcome these limitations but have their drawbacks. One method embodies radial compression in which the medium in a flexible tube is placed in a chamber and squeezed by pneumatic or hydraulic pressure. An obvious limitation to this method is the durability of the flexible tube, especially when in contact with various solvents used during the chromatographic process.

Other methods use some form of axial compression in which a a member acts on one end of the column bed to compress it. These methods have limitations in that the friction of the packing medium acting on the wall of the column causes somewhat of a compression gradient in the bed, thus resulting in a more tightly packed bed closest to the member end. Another limitation to this method has been pressure so that it is limited in use to only the larger particle size and less efficient packing medium.

It is the purpose of this invention to provide a column so structured as to insure reproducible bed regardless of the particle size of the medium used by nonuniformly decreasing the cross-section of the bed in the axial direction.

It is the further purpose of this invention to also compress the bed from one end in conjunction with decreasing the cross-section of the bed to maintain the bed efficiency over a long period of time and as the column is being used.

SUMMARY OF THE INVENTION

An HPLC column comprising a hollow cylindrical barrel provided with closures (caps) at its opposite ends defining therewith a closed chamber for receiving a packing bed of liquid chromatography particulate material, said closures containing openings and, respectively, an inlet opening at one end and an outlet opening at the other end, an elongate plunger mounted in the barrel with its ends extending therefrom, said plunger being movable axially within the barrel and embodying an axially-extending tapered portion extending from the inlet end toward the outlet end and means at one end of the plunger closest to the outlet end of the barrel and extending therefrom operative to move the plunger axially within the chamber to adjust the compaction of the particulate material within the closed chamber.

In an improved version of the HPLC column according to this invention, a cylinder moveable within the barrel is also provided to urge one end of the media bed within the barrel towards the other end of the barrel. As shown in the improved embodiment, the cylinder is coupled to the plunger (spindle) for movement therewith to apply force to the chromatography media bed.

According to the method of preparing the column for use, the particulate media is introduced into the column about the plunger, the caps secured in place, the bed slowly wetted with solvent appropriate to the type of packing, and the nut located at the end of the plunger is tightened to torque value such that the pressure does not exceed that which would crush the particulate material. In the improved version of this invention, a cycliner is coupled to the plunger and one end of the media bed is in engagement therewith to push on the inlet end of the bed as force is applied to the bed by the tapered plunger as it is moved towards the outlet end of the barrel.

As used herein, the term HPLC column means a high performance liquid chromatography column also sometimes referred to as a high pressure liquid chromatography column. Reference may be had to U.S. Pat. No. 4,582,608 which discloses an HPLC column for information purposes.

BRIEF DESCRIPTION OF THE DRAWINGS

The invention will now be described with reference to the accompanying drawings, wherein:

FIG. 2 is an expanded cross-sectional view of a portion of the end cap at the inlet end of the column of FIG. 1;

FIG. 3 is an expanded cross-sectional view of a flow distributor head at the inlet end which fits into the end cap of FIG. 2;

FIG. 4 is a top plan view of the head shown in FIG. 3;

FIG. 5 is an expanded top plan view of the distributor flow plate at the inlet end of the column shown in FIG. 1;

FIG. 6 is a cross-sectional view taken along line 6—6 in FIG. 5;

FIG. 7 is a bottom plan view of the plate of FIG. 5;

FIG. 13 is an enlarged cross-sectional view with parts broken away of the improved column of FIG. 12;

FIG. 14 is a sectional view taken along line 14—14 of FIG. 13;

DESCRIPTION OF THE PREFERRED EMBODIMENTS

Figure 1:
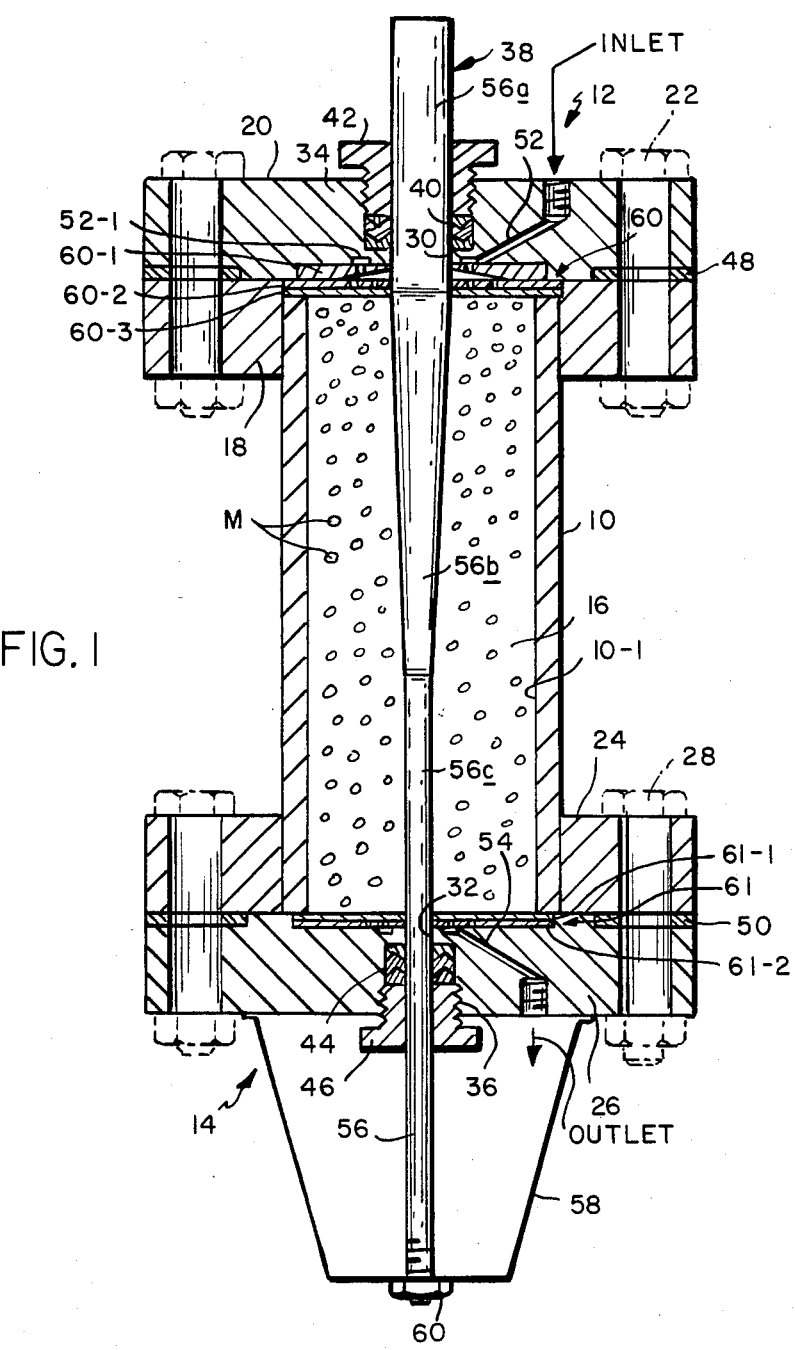
FIG. 1 is a vertical section of the HPLC colums disposed in a position with its inlet end at the top of the figure and its outlet end at the lower end portion of the figure.

Referring to the drawings, FIG. 1, the HPLC column according to this invention comprises a hollow cylindrical barrel 10 of uniform inside diameter having an inner wall 10-1 provided with closures 12 and 14 at its upper and lower ends, respectively, which, in conjunction with the inner wall of hollow cylindrical barrel 10, define a closed chamber 16 within which particulate material M is introduced. The barrel at the upper (inlet) end is provided by an annular collar 18 welded thereto and a cap 20 is detachably secured to the collar 18 by bolts 22. Similarly, the barrel at the lower (outlet) end is provided by a welded collar 24 and a cap 26 is secured thereto by bolts 28. Centrally of the cap 20, there is provided an opening 30 and centrally of the cap 26, there is provided an opening 32 in alignment with the opening 30. The caps 20 and 26 are provided with recesses 34 and 36 concentric with the openings 30 and 32. An elongate plunger (spindle) 38 is mounted within the barrel with its opposite ends extending, respectively, through the openings 30 and 32 and is axially supported therein by glands e.g., teflon ring comprising a packing 40 disposed in the recess 34 and held therein by a threaded nut 42 and a packing e.g., teflon ring 44 held in the recess 36 by a nut 46. Gaskets 48 and 50 are disposed between the respective collars and caps.

The upper cap 20 is provided with an inlet passage 52, the inner end of which terminates close to the axis of the plunger (spindle) 38 and the cap 26 is provided with an outlet passage 54, the inner end of which is closely adjacent the axis of the plunger. Desirably, distributors 60 and 61 are recessed into the caps at the opposite ends of the barrel to insure inform distribution and collection of the solvent as is conventional. See for example U.S. Pat. No. 4,582,608 for a typical distributor.

In accordance with the invention, the spindle (plunger) 38 is provided with portion 56a which extends through the cap 20. A tapered e.g., conical portion 56b having about 3.02° of taper and which extends from the cylindrical portion 56a partway through the chamber and a cylindrical portion 56c of smaller diameter than the cylindrical portion 56a extending the remainder of the way through the chamber and through the cap 26. The tapered e.g., conically-shaped portion 56b of the plunger is located centrally of the barrel within the column of particulate medium (media) contained therein comprising the bed of packing disposed therein and provides, when adjusted axially within the column, for applying pressure to the particulate medium (media) both radially and axially and has for its purpose the achievement of a uniform and reproducible packing of the particulate material. To effect longitudinal movement of the spindle (plunger) 38 and, hence, adjustment of the packing pressure, the spindle has at its lower end, externally of the barrel, a threaded portion 56 about which there is disposed a shroud 58, one end of which bears against the cap 26 and the other end of which contains an opening through which the threaded portion 56 extends and to which a nut 60 is applied. By rotating the nut 60, the spindle may be drawn downwardly within the barrel to exert both axial and radial pressure on the particulate material within the barrel.

The particulate material is introduced into the barrel about the spindle, the end caps secured in place and the bed of particulate material slowly wetted with a solvent appropriate to the type of packing, whereupon the nut 60 is tightened to a torque value such that the pressure on the packing media does not exceed 300 pounds per square inch or other predetermined value to prevent crushing of the particulate material. The forces created by the conical plunger have both vertical and horizontal components which result in a very uniform and reproducible packed bed.

Reference should now be had to FIGS. 2 to 7 which illustrates the member 20 and shows the inlet 52 for fluid entering the column, the inlet having a circumferential channel 52-1 which provides fluid to the distributor 60. The distributor 60 comprises a head 60-1 which has holes 60-1a in alignment with channel 52-1 and a dome shaped portion 60-1c. The fluid passes through the holes 60-1a and is then applied to the distribution plate 60-2 top having the holes 60-2a at a position of the plate offset from the holes 60-2a so that the fluid dosen't go directly through hole 60-1a and then directly through holes 60-2a. Thereafter the fluid containing the sample passes into distribution channels 60-2b aligned with the holes 60-2a and hence through a conventional frit plate (disc) 60-3 e.g. a conventional scintered type having a 2 porosity such as may be purchased from Mott Metalurgical Farmington, Conn.

Figure 8:
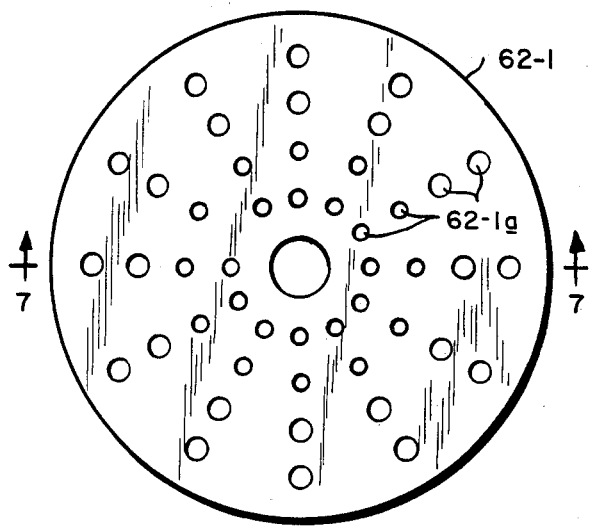
FIG. 8 is an expanded top plan view of the distributior support plate at the outlet end of the column of FIG. 1.
Figure 9:
FIG. 9 is a sectional view taken along line 9—9 in FIG. 8.
Figure 15:
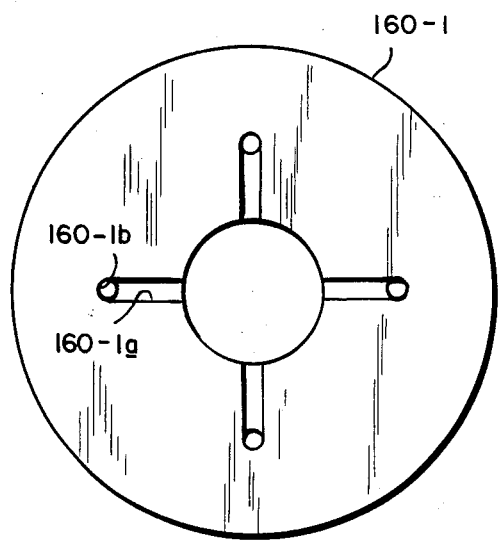
FIG. 15 is a top plan view of the flow distributor head of FIG. 12.
Figure 10:
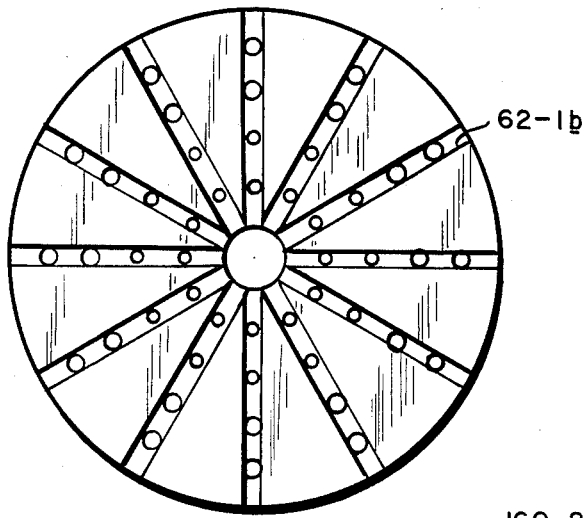
FIG. 10 is a bottom plan view of the distributor plate shown in FIG. 8.
Figure 16:
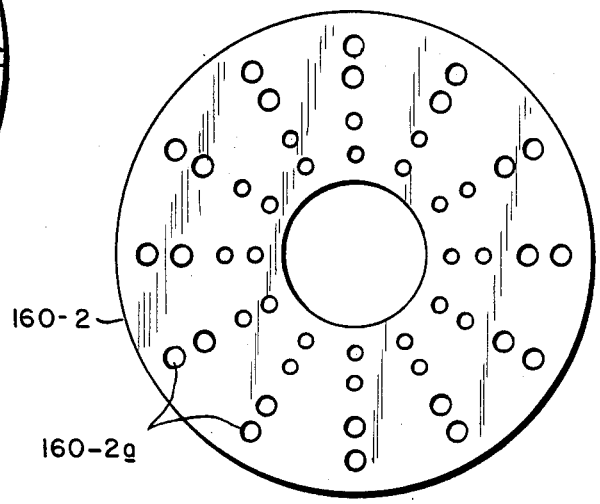
FIG. 16 is a top plan view of the flow distributor plate of FIG. 12.

FIGS. 8 to 10 illustrate the support plate 61-1 (at outlet end) having holes 61-1a on the side facing the particulate media bed M. Fluid from the bed first passes through a frit or scintered porous disc 61-1 e.g. 2 porosity in contact with the support plate 61-1 (see FIG. 1). Fluid from the channels 61-2b passes into the outlet 54 via circumferential channel 54-1.

It should be understood that the exact nature of the inlet distributor 60 and the outlet distributor 61 can vary as would be apparent to those skilled in the art.

Figure 11:
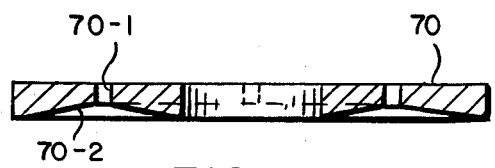
FIG. 11 is a cross-sectional view of a different flow distribution head to take the place of the head shown in FIGS. 3 and 4.

In FIG. 11, there is shown yet another distributor head with holes 70-1 having a ring like circumferential dome 70-2 which can be used in the aforementioned column incorporating the packing apparatus of this invention.

Reference should now be had to FIGS. 12 to 16 which illustrates an improved version of the HPLC column previously described.

In these FIGS. 12 to 16, the HPLC column comprises a hollow cylindrical barrel provided with closures at its opposite ends defining therewith a closed chamber for receiving a packing bed of particulate material (media bed). The closures contain centrally-located, axially-aligned openings and an outlet at one end, an elongate plunger (spindle) mounted in the barrel with its ends extending therefrom through said axial openings. Gaskets are disposed in the openings about the plunger, said plunger being movable axially within the barrel and embodying an axially-extending conical portion coupled to a cylindrical segment at the inlet end. The plunger extends from the inlet end toward the outlet end and there is provided means at one end of the plunger externally of the cap at that end operative to move the plunger and cylindrical segment axially within the chamber to adjust the compaction of the particulate material within the chamber and means at the opposite end of the plunger to provide an inlet for solvent and sample flow. The means for effecting axial movement of the plunger comprises a thread on the plunger externally of the one end, and a nut threaded onto the threaded end of the plunger against the piston. The cylindrical segment at the inlet end of the plunger preferably includes two split teflon guide-rings and a high pressure teflon graphite piston seal which make intimate contact with the internal wall of the hollow cylindrical barrel wall and means to provide inlet for an evenly distributed flow over the top of the packing bed. Gasketing is preferably provided by recesses concentric with the openings within which sealing elements are disposed and held compacted about the plunger by nuts threaded into the recesses against the gaskets.

Figure 12:
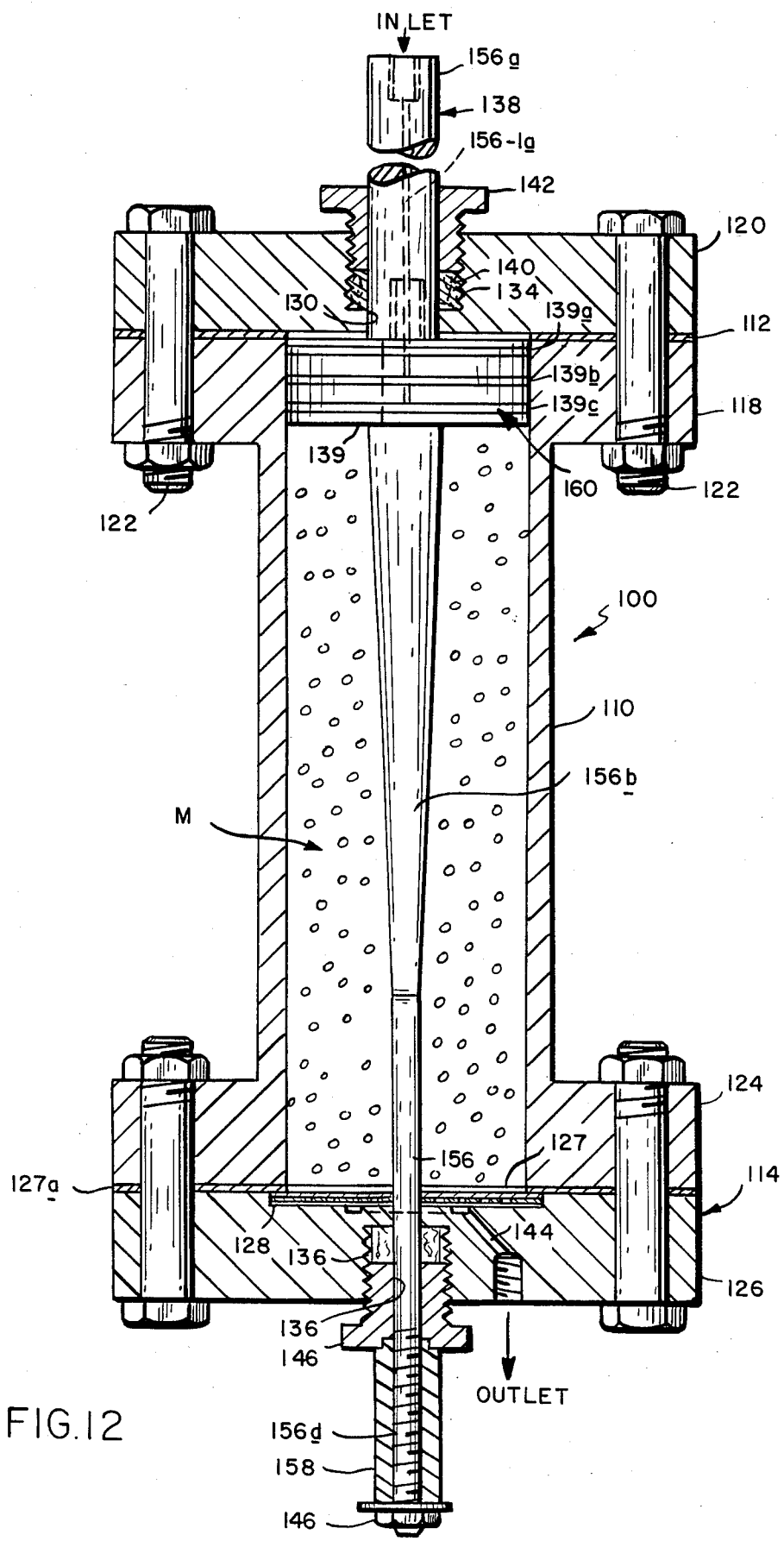
FIG. 12 is a cross-sectional view of an improved HPLC column according to the invention.

According to the method of preparing the column for use, the plunger along with the inlet end cap is secured in place, the column is inverted, the particulate media is introduced into the column about the plunger with the outlet cap removed and then the outlet and cap is secured, the column returned to its normal upright position (as shown in FIG. 12) the bed slowly wetted with solvent appropriate to the type of packing and the nut located at the end of the plunger is tightened to torque value such that the pressure does not exceed that which would crush the particulate material as the cylinder (cylindrical segment) and plunger are drawndownwardly.

More particularly, these FIGS. 12 to 16 shown an HPLC column 100 according to this invention comprises a hollow cylindrical barrel 110 of uniform inside diameter provided with closures 112 and 114 at its upper and lower ends, respectively, which, in conjunction with the hollow cylinderical barrel 110; define a closed chamber 116 within which particulate material M is introduced. The barrel 110 at the upper end is provided with an annular collar 118 welded thereto and cap 120 is detachably secured to the collar by bolts 122. Similarly, the barrel at the lower end is provided by a collar 124 and a cap 126 is secured by bolts 128. Centrally of the cap 120, there is provided an opening 130 and centrally of the cap 126, there is provided an opening 132 in alignment with the opening 130. The caps 120 and 126 are provided with recesses 134 and 136 concentric with the openings 130 and 132. An elongate plunger (spindle) 138 with a cylinder 139 coupled thereto is mounted within the column 110 with the opposite ends of the plunger 138 extending, respectively, through the openings 130 and 132 and is axially supported by glands comprising a packing 140 e.g., teflon gasket disposed in recess 134 and held therein by a threaded nut 142 and a packing e.g., of teflon 144 held in recess 136 by nut 146. The cylindrical portion (segment) 139 is fit with guide rings 139a and 139b e.g., teflon O-rings and a piston seal 139c eg., Bal-Seal brand seal made by Bal-Seal Engineering of Santa Ana, Calif. Sealing gaskets are disposed between the respective collars and caps.

The lower cap 126 is provided with an outlet passage 154, the inner end of which is closely adjacent the axis of the plunger. The outlet cap 126 is also provided with a recess to accept a porous scintered element 127 and a support plate 128 to provide containment of the packed bed and uniform exit of solvent. Further, scintered element 127 is provided with a hole fit with a teflon-graphite "Hat" seal 127a which effectively prevents leakage of packing media and solvent around the plunger portion 156c.

In accordance with the invention, the spindle (plunger) 138 is composed of four separate segments: a cylindrical portion 156a which extends through the cap 120 and provides an inlet; a tapered portion 156b e.g., conically shaped; a cylindrical portion 156c of smaller diameter than the cylindrical portion 156d extending the remainder of the way through the chamber and through the cap 126; and cylindrical portion 139 providing containment of the packed bed e.g., of silicia chromatography media and means 160 for uniform distribution of the solvent finally through a scintered element 139d which is a part of the cylindrical portion 13. The spindle portion comprised of segments 156b and 156c is provided with a means e.g., threaded portion to attach tightly to segment 156a passing through the center of cylinder 139 holding it secure with all of its elements and providing a means to 156a-1 to introduce the solvent to the distribution portion of cylinder 139. Gasketing is provided to insure a liquid tight seal between the segment 156a, cylinder 139 and segment 156b. The tapered or conically-shaped portion 156b is located centrally of the barrel along with the cylindrical portion 139. When adjusted axially within the column, the plunger portion 156b and the cylinder 139 for applying pressure to the particulate medium both radially and axially and has for its purpose to achieve a tightly packed bed i.e., packing of the particulate material. To effect longitudinal movement of the plunger 138 and, hence, adjustment of the packing pressure, the plunger has at its lower end, externally of the barrel, a threaded portion 156 about which there is disposed a hollow cylinder 158, one end of which bears against the nut 146 and other end through which the threaded portion 156 extends and to which a nut 160 is applied. By rotating the nut 160, the spindle may be drawn downwardly within the barrel to exert both radial and axial forces on the particulate material within the barrel.

With the column in an inverted postion and inlet end cap 120 and plunger (spindle) 138 secure, the particulate material is introduced into the barrel about the spindle. The outlet end cap 126, along with all other elements, is secured and the particulate material slowly wetted with a solvent appropriate to the type of packing, whereupon the nut 160 is tightened to a torque value such that the pressure on the packing media does not exceed 300 pounds per square inch or other predetermined value to prevent crushing of the particulate material. The forces created by the cylinder which applies a force vertically through the scintered plate as it is moved downwardly with the spindle to which it is coupled to movement therewith and by the plunger which applies both vertical and horizontal force components results in a very uniform and reproducible packed bed.

In FIGS. 13, 14 15 and 16 there is shown the means 160 for distribution of fluid from the channel 156-2a and channel 156-2b onto the media bed M. The fluid from channel 156-2b passes into the channel 160-1b and then through holes 160-1a of the head 160-1. Thereafter the fluid to be separated by the bed is directed against the plate 160-2 and moves through holes 160-2a thereof into the cylinder 139 channels 160-1b onto the scintered porous plate 139d and then onto the bed M. See FIGS. 5 to 7 for more detail of a plate. At the outlet end of the frit or scintered disc is shown at 127 and the support plate is shown at 128 and is of the same type as disclosed in FIGS. 1 to 10. Fluid passes through holes 128-1 on the top and then into channels 128-2 which communicate with circumferential channel 154-1 of outlet 154. A suitable taper or the conical portion 156-b of the plunger is about 2.20°.

It should be understood that the present disclosure is for the purpose of illustration only and includes all modifications or improvements which fall within the scope of the appended claims.

What is claimed is:

1. An HPLC column comprising a hollow, cylindrical barrel, inlet and outlet caps at the opposite ends of the barrel secured to the ends thereof and defining in conjunction therewith a closed chamber having a bed of particulate material confined within the barrel, a plunger disposed in the barrel with its opposite ends extending from the caps, said plunger being movable axially in the barrel through the caps, said plunger embodying a conical portion extending from the inlet cap thereof partially toward the outlet cap and means at one end of the plunger situated externally of the outlet cap operative to move the plunger axially in the chamber to adjust the compression of the particulate material within the chamber.

2. An HPLC column according to claim 1 wherein the ends of the plunger protrude from the ends of the barrel and there is a nut threaded onto one of the protruding ends of the plunger in engagement with the closure at that end operable to effect axial movement of the spindle in the barrel.

3. An HPLC column according to claim 1 wherein the barrel is filled with particulate material compacted axially and radially at a pressure not exceeding the crush resistance of the particulate material to the pressure applied.

4. The method of providing for uniform distribution of fluid in an HPLC column comprising providing a hollow cylindrical housing supporting a spindle of conical configuration at the longitudinal axis of the housing, filling the housing with particulate material and moving the spindle within the housing in a direction to apply pressure to the particulate in axial and radial directions.

5. An HPLC column comprising a hollow barrel having a bed of particulate material and having first and second ends, a cylinder positioned at or near a first end of the barrel and moveable in the barrel, a plunger coupled to the cylinder for movement therewith, said plunger portion closest to said cylinder being conical with the larger diameter thereof being closest to the cylinder and a cylindrical portion extending from the tapered portion, and first means located at the second end of the barrel for moving said plunger and cylinder in said barrel.

6. An HPLC column comprising a hollow barrel having first and second ends, a cylinder positioned at or near a first end of the barrel and moveable in the barrel, a plunger coupled to the cylinder for movement therewith, said plunger portion closest to said cylinder being conical with the larger diameter thereof being closest to the cylinder and a cylindrical portion extending from the tapered portion, and first means located at the second end of the barrel for moving said plunger and cylinder in said barrel, said cylinder further including means for receiving fluid and providing fluid to the barrel portion on the side of the closest to said conical portion of said plunger and means for removing fluid from the barrel portion on the side of the furthest to said conical portion of said plunger.

7. The column of claim 6 having chromatography media positioned in said barrel between said cylinder and said first means and whereby movement of said cylinder towards said first means with said plunger causes said media to be packed into the space between said cylinder and said first means.

8. An HPLC column according to claim 6 in which said plunger has a portion which is at least partially threaded at the end thereof farthest from the conical portion and a nut forming a part of said first means and coupled to said threaded portion of said plunger for moving said plunger and cylinder in said barrel upon rotation of said nut.

9. An HPLC column according to claim 8 wherein said first means includes means for receiving fluid from the interior of said barrel and providing the fluid to an outlet thereof.

10. A method of packing chromatography media in an HPLC column between two ends and an inner wall thereof, said method comprising placing a plunger having a conical portion and a cylindrical portion centerally into one end of the bed with the plunger taper shaped to cause it when moved towards the other end of the bed to urge the media bed in contact with the taper against the inner walls of the column and towards the end of said column farthest from said plunger taper and moving said plunger towards the end of said column farthest from said plunger taper.

11. The method of claim 10 in which said method includes moving a cylinder against the end of the media bed closest the plunger taper to also urge said media bed towards the end of said column farthest from said plunger taper.

* * * * *